United States Patent [19]
Henderson et al.

[11] Patent Number: 5,874,097
[45] Date of Patent: Feb. 23, 1999

[54] COMPOSITIONS AND METHODS FOR DETECTING AND KILLING TERMITES

[75] Inventors: Gregg Henderson, St. Gabriel; Jian Chen; Roger A. Laine, both of Baton Rouge, all of La.

[73] Assignee: Board of Supervisors of Louisiana State University and Agricultural and Mechanical College, Baton Rouge, La.

[21] Appl. No.: 988,911

[22] Filed: Dec. 11, 1997

[51] Int. Cl.$^6$ .................................................. A01N 25/00
[52] U.S. Cl. ................................. 424/405; 424/DIG. 11; 514/762; 514/763; 514/764
[58] Field of Search ............................ 424/DIG. 11, 405; 514/762, 764, 763

[56] References Cited

U.S. PATENT DOCUMENTS

| | | | |
|---|---|---|---|
| 3,249,501 | 5/1966 | Lund | 424/405 |
| 3,972,993 | 8/1976 | Kobayashi et al. | 424/15 |
| 4,325,993 | 4/1982 | Schroder | 427/315 |
| 4,921,696 | 5/1990 | Vander Meer et al. | 424/84 |
| 4,965,286 | 10/1990 | Krüger et al. | 514/514 |
| 5,185,164 | 2/1993 | Valentincic et al. | 426/1 |
| 5,611,846 | 3/1997 | Overton et al. | 96/102 |
| 5,637,298 | 6/1997 | Stowell | 424/84 |

OTHER PUBLICATIONS

WHO Publication p. 9 1991 Air Quality.
Osha Standards—Toxic and Hazardous Substrates pp. 504–507 1976.
M. Tokoro et al., "Isolation and primary structure of trail phermone of the termite, *Coptotermes formosanus* Shiraki (Isoptera: Rhinotermitidae)," *Wood Res.*, vol. 76, pp. 29–38 (1989).
F. Matsumura et al., "Isolation and Identification of Termite Trail–Following Pheromone," *Nature*, vol. 219, pp. 963–964 (1968).
N. Laduguie et al., "Isolation and Identification of (3Z,6Z,8E)–3,6,8–dodecatrien–1–ol in *Reticulitermes santonensis* Feytaud (Isoptera, Rhinotermitidae): Roles in Worker Trail––Following and in Alate Sex–Attraction Behavior", *J. Insect Physiol.*, vol. 40, pp. 781–787 (1994).
G. Prestwich et al., "Structure–activity relationships among aromatic analogs of the trail–following pheromone of subterranean termites," *J. Chem. Ecol.*, vol. 10, pp. 1201–1217 (1984).
G. Becker et al., "Untersuchungen über das verhalten von Termiten gegenüber einigen spurbildenden Stoffen," *Z. Angem. Entomol.*, vol. 53, pp. 400–436 (1968). (See English Language summary, pp. 433–434.).

M. Rust et al., "Enhancing Foraging of Western Subterranean Termites (Isoptera: Rhinotermitidae) in Arid Environments," *Sociobiology*, vol. 28, pp. 275–286 (1996).
J. Gassett et al., "Volatile Compounds from the Forehead Region of Male White–Tailed Deer (Odocoileus virginianus)," *J. Chem. Ecol.*, vol. 23, pp. 569–578 (1997).
J. Chen et al., "Naphthalene in Formosan Subterranean Termites and Their Nest Carton," Poster Presentation, 213th American Chemical Society National Meeting (San Francisco, CA, Apr. 1997).
G. Henderson, "No Fungus Among Us," *PCT Pest Control Technology*, pp. 60–61 (May 1997).
B.M. Spears et al., "Survival and Food Consumption by the Desert Termite *Gnathamitermes tubiformans* (Buckley) in Relation to Dietary Nitrogen Source and Levels," *Environ. Entomol.*, vol. 5, pp. 1022–1025 (1976).
J.S. Shellman–Reeve, "Dynamics of Biparental Care in the Dampwood Termite, *Zootermopsis nevadensis* (Hagen): Response to Nitrogen Availability," *Behavioral Ecology and Sociobiology*, vol. 26, pp. 389–397 (1990).
R.E. Hungate, "Experiments on the Nitrogen Economy of Termites," *Ann. Entom. Soc. Am.*, vol. 34, pp. 467–489 (1941).
Su et al., "Laboratory Evaluation of Two Slow–Acting Toxicants Against Formosan and Eastern Subterranean Termites (Isoptera:Rhinotermitidae)," *J. Economic Entomology*, vol. 84(1), pp. 170–175 (1991).
Yaga, S., "On the Secretion of Termites *Copotatermes formosanus* Shiraki, The Components of Sugars and Amino Acids in the Secretion of Workers," *The Science Bulletin of the College of Agriculture*, University of Ryukyus, Okinawa, No. 19, pp. 481–488 (1972).
Osmun, J. V., "Household Insects," Pfadt (ed.), *Fundamentals of Applied Entomology*, MacMillan Publishing Co., Inc., New York, pp. 543–544 (1971).

*Primary Examiner*—Neil S. Levy
*Attorney, Agent, or Firm*—John H. Runnels

[57] ABSTRACT

Significant concentrations of naphthalene were detected in carton nests of Formosan subterranean termites, *Coptotermes formosanus* Shiraki, collected from Florida, Hawaii, and Louisiana. This is the first report of naphthalene being associated with termites or any other insects. Naphthalene and other compounds associated with termite carton nests may be used to increase termite bait acceptance. New attractant molecules include 2-phenoxyethanol. New feeding stimulants include ergosterol. A list of volatile compounds associated with termite nests is presented, compounds that may be used to detect termite nests.

15 Claims, No Drawings

COMPOSITIONS AND METHODS FOR DETECTING AND KILLING TERMITES

This invention pertains to compositions and methods for detecting and killing termites.

The Formosan subterranean termite, *Coptotermes formosanus* Shiraki, is a major worldwide pest that attacks both living trees and structural wood. Unlike other subterranean termites, the Formosan termite can establish a colony that does not touch the ground.

*Coptotermes formosanus* is native to southeast Asia, but is now also found in Hawaii, along the southeastern Atlantic coast of the United States, and in the Gulf South of the United States. First discovered in the United States in 1965, *C. formosanus* has gradually expanded its geographic domain. The largest single locus of *C. formosanus* in the United States is in south Louisiana, with heavy infestations in Lake Charles and New Orleans. *C. formosanus* may in some cases displace native Reticulitermes spp.

*C. formosanus* continues to cause great structural damage to many buildings in the Lake Charles and New Orleans areas, including damage to many buildings of historic significance. There is particular concern for the future of New Orleans' French Quarter, where many historic buildings are already severely damaged and would be quite expensive to repair.

Three principal methods have been used in the past to control *Coptotermes*: (1) chemical and physical barriers to prevent termites from attacking wood, (2) wood preservatives and termiticides used to protect infested or susceptible wood, and (3) destruction of a termite colony by excavation of the nest.

Chemical barriers and termiticides have generated public concern over environmental safety.

In China excavation of the nest has been one of the main methods used to control Formosan termites. However, locating a termite nest is typically very time-consuming, limiting the usefulness of the practice.

Using a bait to deliver a termiticide has several advantages. Baits typically require only a small amount of the toxicant, and they target only the insects that feed on the bait (or are re-fed the bait by nest mates). Thus non-target organisms are not affected, diminishing the environmental impact of the toxicants. Use of a bait can make it unnecessary to locate the nest, because many termites, including Formosan termites, engage in trophallaxis (transfer of food to other colony members). Thus the toxicant may be spread throughout a colony after feeding by only a few foraging termites. Bait methods have previously been used to detect and experimentally control subterranean termites, and to trap termites for studies on termite ecology.

A major problem with existing baiting techniques against Coptotermes species has been inconsistent bait acceptance. Baits placed within termite galleries are often bypassed and left uneaten. The use of termite baits is different from the use of ant baits and cockroach baits, because it is usually not possible to remove competing food sources for termites. Attractants and feeding stimulants have sometimes increased the consistency of bait acceptance, but there remains a continuing need for improved termite baits.

There is a continuing need for improved techniques for killing termites. There is also a continuing need for improved methods for detecting termite nests. Current detection techniques rely primarily on visual inspection. Unfortunately, termite nests are frequently overlooked by visual inspection techniques. Formosan termite nests, in particular, can often be outwardly invisible for years, while the termites cause considerable unseen damage.

*C. formosanus* uses soil, masticated wood, and excrement, cemented by saliva and excrement, to make its nests, termed "cartons." Gallery and shelter tube systems connect primary nests to accessory nests and feeding sites. *C. formosanus* colonies continually expand their foraging areas by enlarging the nest, or by building accessory nests.

J. Chen et al., "Naphthalene in Formosan Subterranean Termites and Their Nest Carton," Poster Presentation, 213th American Chemical Society National Meeting (San Francisco, Calif., April 1997) presented some of the results disclosed in the present specification.

U.S. Pat. No. 5,637,298 discloses that 2-naphthalenemethanol and certain derivatives of 2-naphthalenemethanol are termite attractants, and that these attractants may be used to increase bait acceptance by termites.

G. Henderson, "No Fungus Among Us," PCT Pest Control Technology, pp. 60–61 (May 1997) states that four unidentified chemicals used by Formosan termites to inhibit fungal growth had been identified, and that the chemicals were toxic to ants.

Both the introduced Formosan subterranean termite, *Coptotermes formosanus* Shiraki, and subterranean termites in the genus *Reticulitermes* exhibit trail-following behaviors. M. Tokoro et al., "Isolation and primary structure of trail pheromone of the termite, *Coptotermes formosanus* Shiraki (Isoptera: Rhinotermitidae)," Wood Res., vol. 76, pp. 29–38 (1989) reported isolation of the trail pheromone from *C. formosanus*, and identified it as (Z,Z,E)-3,6,8-dodecatrien-1-ol (DTE-OH), which has also been reported to be the trail-following pheromone of *R. virginicus* (Banks) and *R. santonensis* (Feytaud). See F. Matsumura et al., "Isolation and Identification of Termite Trail-Following Pheromone," Nature, vol. 219, pp. 963–964 (1968); and N. Laduguie et al., "Isolation and Identification of (3Z,6Z,8E) -3,6,8-dodecatrien-1-ol in *Reticulitermes santonensis* Feytaud (Isoptera, Rhinotermitidae): Roles in Worker Trail-Following and in Alate Sex-Attraction Behavior," J. Insect Physiol., vol. 40, pp. 781–787 (1994).

Termites have also showed trail-following activity in response to certain non-pheromone chemicals. The trail-following activity of several synthesized (Z)-4-phenyl-3-buten-1-ol derivatives has been tested for five species of subterranean termites in the genera of *Coptotermes, Reticulitermes*, and *Schedorhinotermes*. See G. Prestwich et al., "Structure-activity relationships among aromatic analogs of the trail-following pheromone of subterranean termites," J. Chem. Ecol., vol. 10, pp. 1201–1217 (1984).

Several glycol compounds have been reported to act as trail following substances for termites. G. Becker et al., "Untersuchungen über das verhalten von Termiten gegen über einigen spurbildenden Stoffen," Z. Angem. Entomol., vol. 53, pp. 400–436 (1968). (See English language summary, pp. 433–434.)

M. Rust et al., "Enhancing Foraging of Western Subterranean Termites (Isoptera: Rhinotermitidae) in Arid Environments," Sociobiology, vol. 28, pp. 275–286 (1996) reported that foraging of the western subterranean termite *Reticulitermes hesperus* was enhanced by placing into sand extracts from the brown rot fungus *Gloeophyllum trabeum*, and that the fungal extract plume in the soil could assist worker termites in locating monitoring or bait stations.

J. Gassett et al., "Volatile Compounds from the Forehead Region of Male White-Tailed Deer (*Odocoileus virginianus*)," J. Chem. Ecol., vol. 23, pp. 569–578 (1997) reported several compounds identified in secretions from the forehead and back of the male white-tailed deer, including naphthalene.

Papermate® ball-point pen ink is known to elicit trail following behaviors in introduced Formosan subterranean termites and native subterranean termites. (Harry McMennemy, private communication.) However, the active ingredient has not previously been identified.

We have discovered several previously unknown components of termite nest cartons. These compounds may be used as an attractant for termite baits, as a feeding stimulant, as the basis for novel chemical methods of detecting termite nests, and as the basis for novel biological methods of controlling termites.

As one example of these newly-discovered components, we have for the first time identified and quantitatively measured naphthalene as a compound present in termite cartons. Naphthalene has been identified in colonies from Florida, Hawaii, and Louisiana by gas chromatography-mass spectrometry (GC-MS).

EXAMPLE 1

Termites and nest carton materials.

Termites with their nest cartons were collected from colonies infesting houses and trees in New Orleans, Lake Charles, Houma, Slidell, Algiers, and Gretna, Louisiana. Collected termites were kept at room temperature (23°–28° C.) in plastic or aluminum trash cans with pine wood stakes and corrugated cardboard. Nest carton from a colony in Honolulu, Hawaii was provided by Dr. J. K. Grace and Mr. J. Wang. Nest carton from a colony in Largo, Fla. was supplied by Mr. G. D. Gordon. The cartons from Hawaii and Florida were stored at 4° C. until analysis.

EXAMPLE 2

Measurement of naphthalene in termite nest carton.

Naphthalene was quantitatively measured in the colonies of Example 1 from Florida, Hawaii, and New Orleans, Louisiana. One-half kilogram carton material from the Hawaiian or Louisiana carton, and all of the available carton from the Florida collection (about 400 g each) were ground into a powder using a ceramic mortar and pestle. Three 50-gram sub-samples were extracted with 50 mL hexane three times; and 50 $\mu$L azulene (99+%, Sigma Chemical Co., St. Louis, Mo.) in hexane solution at a concentration of 0.178 mg/mL were added to each sample as an internal standard. The pooled extract was concentrated to 0.1 lmL using a rotary evaporator and nitrogen flow. The extract was then analyzed by GC-MS. As a control, 150 mL of hexane were concentrated to 0.1 mL and analyzed for naphthalene. Rates of loss by evaporation were equivalent for azulene and naphthalene.

Nest carton material from five Louisiana colonies (one each from Algiers, Houma, and Slidell, and two colonies from New Orleans) were qualitatively analyzed for naphthalene. Six hundred grams of carton material from each colony were ground and extracted with 350 mL hexane three times. Pooled extracts were concentrated to 1.5 mL with a rotary evaporator and nitrogen flow, and were filtered with hexane through a 5 cm×0.3 cm silica gel, 70–230 mesh (63–200 $\mu$m), average pore diameter: 60 Å, Sigma Chemical Co., St Louis, Mo.). The first 4 mL were collected, concentrated to 0.3 mL under nitrogen flow, and analyzed by GC-MS. One thousand fifty mL of hexane were concentrated to 0.3 mL and analyzed as a control for naphthalene in the solvent.

The naphthalene retention time was 7.85 min. with the GC-MS system described below. Naphthalene levels in carton nests ranged from about 100 $\mu$g/kg in Louisiana colonies, to about 250 $\mu$g/kg in Hawaiian colonies, to about 500 $\mu$g/kg in Florida colonies. The mass spectrum and GC retention time of 7.85 minutes both matched a naphthalene standard. Naphthalene was not detected in the solvent control samples, but was found in nest carton materials from all five colonies analyzed.

Following is a description of the analytical techniques used in this Example 2. Unless otherwise indicated, generally similar analytical techniques were used in the other Examples. Naphthalene analysis of carton nest was conducted by GC-MS using a Hewlett Packard 5890 Gas Chromatograph with a 5971A Mass Selective Detector (a quadrupole mass spectrometer using 70 eV electron impact ionization). The GC was equipped with a DB-5MS column (20 m long, 0.18 mm i.d., film thickness 0.18 $\mu$m, J&W Scientific, Folsom, Calif.). The initial temperature was 50° C. for 3 min., programmed at 20° C./min. to 280° C., which was held for 25 min.

Naphthalene was identified by comparison of mass spectra and GC retention times of peaks in the sample with those of a naphthalene standard (99+%, Sigma Chemical Co., Mo.).

EXAMPLES 3–7

Antifungal Activities of Compounds Associated with Formosan Termites

Five compounds that we isolated from the nests and bodies of Formosan subterranean termites were evaluated to determine their effect on a Mucor spp. fungus that is associated with termites and termite nests. Of the five compounds tested, naphthalene was most effective at inhibiting the growth of this fungus. We believe that one function of naphthalene in termite nests is to inhibit pathogenic fungal growth.

The humid conditions of termite nests and galleries are ideal for the growth of several species of fungi. Some of these fungi are beneficial to termites, aiding in the breakdown of cellulose or providing additional nutrients, while other fungi are toxic or pathogenic to termites. Fungi are found more often in wood with termite galleries than in wood without termite galleries, suggesting that termites both introduce fungi to the wood, as well as help spread fungi that are already present. Mucor species, so-called sugar fungi, are commonly associated with dung, leaf lifter, and other decaying organic matter.

Our research group has often observed a white fungus flourishing on termite nests within one week of our collecting a nest in the field and bringing it into our laboratory. Nests with such visible fungal activity invariably contain large numbers of sick and dying termites. This fungus has presented substantial obstacles to maintaining collected termite colonies in our laboratory for research purposes. We recently identified the fungus as a Mucor spp.

Mucor was isolated from a Formosan termite nest in our laboratory, a nest originally collected from a cottonwood tree in New Orleans, La. The fungus comprised a white mat that covered large areas of the nest that had been exposed to air and water. Fungus was scraped from the nest and suspended in distilled, de-ionized water with a Pasteur pipette. This suspension was streaked on Sabouraud dextrose agar ("SDA") (Difco Laboratories, Detroit, Mich.) in 100×15 mm plates containing 20 mL SDA. Pure cultures were obtained from individual colonies on these plates as needed. Cultures were maintained on SDA plates in a 27° C. incubator without light until used.

Filter paper disks (Whatman #1, 1.5 cm) were treated with naphthalene, butylated hydroxytoluene (BHT), dioctyl phthalate, or adipic dioctyl ester, at rates of 2 μg, 20 μg, or 200 μg, dissolved in 100 μL hexane. Controls were treated with hexane alone. For each treatment, just prior to testing for antifungal properties, 1 mL of the hexane solution and ten filter paper disks were placed in a vial, and $N_2$ was used to evaporate the hexane.

A suspension was prepared by scraping Mucor conidia (spores) from the culture plates, and mixing into distilled, deionized water with a Pasteur pipette. A thin layer of this suspension was spread over the surface of each of 130 SDA plates by placing each plate onto an inoculation turntable (Fisher Scientific, Hampton, N.H.), pipetting 0.2 mL of the suspension into the center of the plate, spinning the turntable, and spreading the suspension onto the agar with a bent glass rod. The plates were allowed to dry for two hours. A treated filter paper disk was then placed in the center of each plate (10 plates/treatment), and the plates were incubated at 27° C. The extent to which each filter paper disk was covered by fungus was determined by visual inspection (by the method described in greater detail below) after four, five, and six days.

A second trial was conducted with filter papers treated with naphthalene, BHT, or 2,6-di-t-butyl-4-methyl-phenol ("DBP"). A fungal suspension was prepared as in the first trial. Spore concentrations were determined with a counting chamber (Petroff-Hauser, Hauser Scientific Partnership, Horsham, Pa.). Concentrations were adjusted to approximately $10^7$ spores/mL. In the first trial fungus grew on SDA quickly, forming a thick mat that soon filled the entire petri dish. Therefore, in the second trial cornmeal agar (CMA, Difco Laboratories, Detroit, Mich.) was used to slow the growth of the fungus during the six-day observation period. A thin layer of the spore suspension was spread over the surface of each of 24 cornmeal agar plates using a turntable and bent glass rod, as previously described.

Filter paper disks were treated with naphthalene, BHT, or DBP at rates of 2 μg, 20 μg, or 200 μg, prepared as in the first trial. On each plate were placed four filter paper disks spaced equidistant from one another (one disk containing each of the three application rates of one of the test compounds, and one disk containing only the hexane control). Each plate was then covered and sealed with parafilm to reduce the release of volatile compounds. The concentration of naphthalene in the headspace was 0.04 μg/cm³; except in trial 3 below, in which the concentration was 34.6 μg/cm³, about 700 times the concentration we have observed in termite nest materials. The growth of fungus on and around each filter paper disk was recorded three, four, and five days after treatment. The experiment was then repeated, increasing the rates of naphthalene, BHT, and DBP to 200 μg, 600 μg, and 1000 μg (trial 3).

Fungal growth on each filter paper disk was recorded by making tracings of the disks, inking in areas with visible fungal growth. The fraction of each disk covered by fungus was measured by making photocopy enlargements of these drawings, cutting out the enlarged disks, weighing the entire circle, cutting out the inked areas of the circle (corresponding to fungal growth), and weighing the latter. The fraction of each circle covered with fungus was then calculated as the ratio of these weights. (The weight of the photocopy toner was negligible.)

Coverage of filter paper disks was analyzed by the ANOVA procedure (SAS Institute, Version 6. 11, Cary, N.C.). Tukey's Studentized Range (HSD) Test was used for comparison of mean separations ($\alpha=0.05$).

In the first trial, the growth of fungus on the treated filter paper disks did not differ significantly from the growth on control disks. See Table 1.

TABLE 1

Mean percentage of filter paper disk surface covered by fungus, trial 1.

| Compound | Rate | Fraction covered, Day 4 | Fraction covered, Day 5 | Fraction covered, Day 6 |
| --- | --- | --- | --- | --- |
| Naphthalene | 2 μg | 71% | 86% | 98% |
|  | 20 μg | 64% | 97% | 100% |
|  | 200 μg | 90% | 92% | 100% |
| BHT | 2 μg | 70% | 85% | 92% |
|  | 20 μg | 27% | 65% | 76% |
|  | 200 μg | 28% | 56% | 93% |
| Dioctyl phthalate | 2 μg | 67% | 78% | 89% |
|  | 20 μg | 32% | 49% | 88% |
|  | 200 μg | 57% | 69% | 82% |
| Adipic dioctyl ester | 2 μg | 44% | 83% | 94% |
|  | 20 μg | 20% | 80% | 62% |
|  | 200 μg | 20% | 75% | 91% |
| Control | 0 μg | 50% | 88% | 93% |

In trials 2 and 3, where conditions favored slower growth, filter papers containing all concentrations of a particular compound were placed onto the same agar plate. Therefore, when comparing the significance of different results from different compounds, all concentrations of the same compound were grouped together and considered as a single treatment. In trial 2, filter paper coverage was greater than 90% after three days for all compounds. See Table 2.

TABLE 2

Mean percentage of filter paper disk surface covered by fungus, trial 2.

| Compound | Rate | Fraction Covered, Day 3 | Fraction Covered, Day 4 | Fraction Covered, Day 5 |
| --- | --- | --- | --- | --- |
| Naphthalene | 0 μg | 98% | 99% | 95% |
|  | 2 μg | 100% | 99% | 100% |
|  | 20 μg | 98% | 98% | 99% |
|  | 200 μg | 100% | 100% | 100% |
| BHT | 0 μg | 93% | 94% | 96% |
|  | 2 μg | 85% | 90% | 90% |
|  | 20 μg | 93% | 95% | 98% |
|  | 200 μg | 95% | 99% | 100% |
| DBP | 0 μg | 96% | 100% | 100% |
|  | 2 μg | 98% | 99% | 99% |
|  | 20 μg | 92% | 95% | 98% |
|  | 200 μg | 81% | 91% | 99% |

In the third trial, where application rates increased to a maximum of 1000 μg, no fungal growth was seen on the filter paper disks for any of the naphthalene treatments. See Table 3. Three days after treatment, coverage of filter paper was significantly greater in the BHT treatments than in either the DBP or naphthalene treatments (P=0.0001). By the fourth day, fungal coverage of both the BHT- and the DBP-treated disks approached 100%, while there was still no growth on the naphthalene treated disks. When plates were examined eight days after treatment, the disks treated with naphthalene were still free of fungus. Since "naphthalene disks" inhibited fungal growth at all rates of application (including the 0 μg application), the fungicidal activity was apparently due at least in part to fumigation by naphthalene vapor, instead of (or perhaps in addition to) contact with the solid phase naphthalene.

TABLE 3

Mean percentage of filter paper disk surface covered by fungus, trial 3.

| Compound | Rate | Fraction Covered, Day 3 | Fraction Covered, Day 4 | Fraction Covered, Day 5 |
|---|---|---|---|---|
| Naphthalene | 0 μg | 0% | 0% | 0% |
| | 200 μg | 0% | 0% | 0% |
| | 600 μg | 0% | 0% | 0% |
| | 1000 μg | 0% | 0% | 0% |
| BHT | 0 μg | 59% | 100% | 100% |
| | 200 μg | 30% | 96% | 95% |
| | 600 μg | 53% | 97% | 100% |
| | 1000 μg | 16% | 99% | 100% |
| DBP | 0 μg | 40% | 100% | 100% |
| | 200 μg | 0% | 94% | 93% |
| | 600 μg | 1% | 100% | 100% |
| | 1000 μg | 0% | 91% | 97% |

EXAMPLE 8

Eliminating Natural Termite Defense Barriers

Although some fungi are beneficial to the termite colony, excessive fungal growth can cause termite death. Combined with other defense mechanisms, such as labial gland secretions, termites may use naphthalene fumigation as an important mechanism to suppress the growth of fungi in their nests. In healthy termite colonies, fungal growth is suppressed, at least in part, by naphthalene in air spaces in the nests. However, in disturbed colonies natural barriers are broken, allowing air to enter the nest more freely. This elimination of a natural defense mechanism explains the fungal mats that we have often seen after colonies have been transported from the field to the laboratory. We propose that one way to exterminate at least some termite colonies is to create conditions encouraging the flow of volatile naphthalene (and perhaps other volatile compounds) away from the termite nest. This goal might be achieved, for example, by one of more of the following techniques: placing many holes in the termite nest, forcing air through the nest with a fan, or forcing water into the nest. These methods of increasing the outward flow of volatile compounds may be used alone, or in conjunction with other methods of exterminating termite colonies.

EXAMPLE 9

2-phenoxyethanol as a trail-following compound

We have isolated and identified 2-phenoxyethanol as the compound in Papermate® ball-point pen ink that elicits trail-following activity in termites. 2-phenoxyethanol elicited trail-following behaviors in both *C. formosanus* Shiraki and *Reticulitermes* spp. Holmgren.

Papermate® ball-point pens were purchased from an Office Depot store in Baton Rouge, Louisiana. *C. formosanus* were collected from a colony in New Orleans, La. *Reticulitermes* spp. were collected from a colony in Baton Rouge, La. Collected termites were kept at room temperature (23°–28° C.) in plastic containers (20 cm diam., 20 cm height) with sand (#4 blasting sand) and moistened corrugated cardboard.

Ink was removed from 30 ball-point pens into 200 mL 5% ethanol. The ink solution was extracted with 200 mL hexane three times. The upper (hexane) layers were collected, filtered through a filter paper (Whatman 1, qualitative, 15.0 cm), and then concentrated to 5 mL under reduced pressure. The extract was placed on a glass column (5 cm long, 2 cm i.d.) packed with silica gel (70–230 mesh, 60 Å average pore diameter, Sigma Chemical Co., St. Louis, Mo.). The column was successively eluted with 100 mL hexane and 400 mL of a 50%/50% mixture of acetyl acetate and hexane. The acetyl acetate-hexane elution was collected and concentrated to 2 mL under reduced pressure. This fraction was further fractionated by high-performance liquid chromatography with a normal-phase Supelcosil™ LC-Si column (25 cm×4.6 mm, 5 μl particle size, 100 Å pore size). Elution was performed with hexane-dichloromethane in gradient mode at a flow rate of 1.0 mL/min. The solvent composition was programmed as follows: 100% hexane for the first 20 min., then changed over 20 min. linearly from 100% hexane to hexane-dichloromethane 90%:10%, then linearly changed over 30 min. from hexane-dichloromethane 90%:10% to 100% dichloromethane, and kept at that composition for 10 min. The column was cleaned by running with 100% dichloromethane for more than 20 min. between runs. One fraction was collected every two minutes (for a total of 40 samples). Each fraction was concentrated into 0.3 mL under nitrogen.

The high-performance liquid chromatograph (HPLC) was a Ranin Rabbit HP/HPX Solvent Delivery System with two Ranin Pump Heads (10 mL). A Knauer Variable Wavelength Monitor was used as a detector. The GC-MS used was a Hewlett Packard 5890 Series II gas chromatograph, coupled with a Hewlett Packard 5971A mass-selective detector. The GC was equipped with a capillary DB-5 column. The injection temperature was 250° C. The oven temperature was kept at 50° C. for the first 2 min., then programmed at 20° C. per min to 280° C., and held at 280° C. for 6.5 min. Helium carrier gas was delivered at a velocity of approximately 40 cm/sec. The ion source temperature was 200° C., and the ionization voltage was 70 eV.

*C. formosanus* workers were used in the initial bioassay for trail-following behavior. The trail-following bioassay was conducted on two overlapped pencil circles of radius 3 cm. The circumference of each circle passed through the center of the other circle. Each sample was streaked along one of the circles with a 4 μl-micropipette on nonabsorptive paper. A solvent (control) was streaked along the overlapping circle. After the solvent evaporated, one worker was placed in the center of overlap between the two circles. The arena was covered with a red plastic container to reduce visible light and extraneous air flow. To score the worker's activity, one point was given for each continuous 3 cm traveled by a termite over a one minute period. Three replications were performed for each fraction. A new termite was used and new circles were drawn for each trial. A fraction was considered inactive if no points were assigned; it was considered moderately active if, on average, termites followed the circle between 3 to 6 cm; and was considered very active if termites followed the trail for 6 cm or more.

HPLC Fraction 34 was moderately active. Fractions 35 to 40 were very active. Eight fractions, numbers 29 to 36, were selected for individual GC-MS analysis to identify increases in the active compound(s) responsible for trail-following activity. This set of neighboring fractions, covering the transition from inactive fractions to active trail-following fractions, was chosen to yield information that could be helpful in identifying the active peak(s), and in ruling out compounds that might co-elute during the active period but that lacked trail-following activity. Compounds were identified by comparing GC-retention times and mass spectra to those of standards.

A peak with retention time 8.10 min. was seen in each of the eight HPLC fractions selected for GC-MS analysis. The 8.10 minute peak was especially strong in fractions 34 to 36. A computer library search, and comparison of mass spectra and retention times with a standard compound, confirmed that this peak was 2-phenoxyethanol.

Trail-following bioassays with standard 2-phenoxyethanol followed procedures that were essentially identical to those for the HPLC fraction screening bioassay described above, except that each trial was replicated 10 times; and that workers and soldiers of both *C. formosanus* and *Reticulitermes* spp. were tested. Four concentrations of 2-phenoxyethanol, 0.32, 0.032, 0.0032, 0.00032 μg/cm were used in the bioassays.

2-phenoxyethanol elicited trail-following behaviors in *C. formosanus* workers and soldiers, and also in *Reticulitermes* spp. workers and soldiers at concentrations of 0.32 μg/cm, 0.032 μg/cm, and 0.0032 μg/cm. Limited trail-following activity at 0.00032 μg/cm was also seen.

2-phenoxyethanol shares little structural similarity to the natural termite trail pheromone of Formosan subterranean termites, except that both are primary alcohols.

EXAMPLES 10–36

Other Potential Attractants, Stimulants, and Reporter Molecules

The molecules identified in Examples 10–73, derived from termite nest carton, are potential termite attractants or feeding stimulants, or potential reporter molecules to identify the presence of termite colonies.

Analyses generally similar to those described above for Examples 1 and 2 have identified several other compounds from termite carton materials, some of which have activity as feeding stimulants, attractants, and defensive chemicals. (Bioactivity testing of these compounds is ongoing.) Compounds that we have identified in Formosan termite nest cartons included arenes, esters, organic acids, sterols, and long-chain hydrocarbons.

The arenes identified included naphthalene and BHT.

The organic acids identified included hexanoic acid; octanoic acid; nonanoic acid; undecanoic acid; nonanedioic acid; dodecanoic acid; tetradecanoic acid; pentadecanoic acid; hexadecanoic acid; heptadecanoic acid; 14-methyl-hexadecanoic acid; (Z,Z)-9,12-octadecadienoic acid; octadecanoic acid; 6-octadecenoic acid; 2-octyl-cyclopropaneoctanoic acid; eicosanoic acid; docosanoic acid; and tetracosanoic acid.

Sterols identified include 3-β-dihydrocholesterol; (24s)-stigmast-5-en-3-ol; and methyl (3-β-5-α)ergostan-3-ol. A feeding bioassay on an ergosterol standard showed that ergosterol also stimulated the feeding of Formosan termites. The bioassay was conducted according to the general procedures of U.S. application Ser. No. 08/243,950, filed May 17, 1994.

Esters identified include hexanedioic acid dioctyl ester; dioctyl phthalate; and dibutyl phthalate.

EXAMPLES 37–73

Solid Phase Extraction of Nest Carton Components

Microwave Distillation-Solid Phase Microextraction (MD-SPME) combined with gas chromatography-ion trap mass spectrometry was also used to extract and identify components of nest carton, using a modification of an analytical technique developed by S. W. Lloyd and C. C. Grimm of the Southern Regional Research Center, United States Department of Agriculture, Agricultural Research Service.

Twenty five grams of carton material were placed in a 100 mL round bottom flask inside a standard 800 W microwave oven. A double offset inlet adapter was connected to the flask. Each opening on the adapter held a Teflon™ tube. Both tubes exited through a hole in the side of the oven. One tube was connected to a nitrogen gas cylinder, and the other was inserted into a 20 mL graduated cylinder placed in a −14° C. cooler. The oven ran at 50% power for 3 min. to heat the sample, while nitrogen flowed through the flask at 80 mL per minute. The volatilized components and water vapor condensed in the −14° C. 20 ml graduated cylinder. The condensate was diluted to 8 mL with water, and poured into a 10 mL vial along with 3.0 g NaCl and a stir bar. The vial was then covered with Teflon tape and placed in a 40° C. water bath with magnetic stirring. A solid-phase microextraction fiber (Sulpelco, Inc., Bellefonte, Pa.) with a 100 μm polydimethylsiloxane phase was exposed to the headspace in the vial for 30 min. A GCQ™ gas chromatography-mass spectrometer was used to analyze the volatiles. The results appear below, with the most likely candidates for each peak identified by a computerized library search against measurements of known standards.

TABLE 4

| Peak number, Retention time (min) | Probable composition |
| --- | --- |
| 1, 3:55 | Ethanedione, diphenyl- |
|  | Benzoyl isothiocyanate |
|  | Benzoyl chloride |
| 2, 5:50 | Benzene (methoxymethyl) |
|  | Phenylethyl alcohol |
|  | Benzalhebyde, 3-benzyloxy-2-fluro-4-methoxy- |
| 3, 6:20 | 1,3-Dioxolane, 4-pentyl-5-propyl-2, 2-bi(trifluoromethyl)-, cis- |
|  | Cis-9, 10-Epoxyoctadecan-1-ol |
|  | Cyclopentane, 1-hexyl-3-methyl- |
| 4, 6:43 | 2-Furanmethanol, 5-ethenyltetrahydro-α, α, 5-trimethyl- |
|  | 6-Nonynoic acid, methyl ester |
|  | 3-Nonynoic acid, methyl ester |
| 5, 7:48 | (R)-(−)-(2)-14-methyl-8-hexadecen-1-ol |
|  | (Z)-6-pentadecen-1-ol |
|  | 9-Eicosyne |
| 6, 7:58 | 2,5-Heptadien-4-one, 2,6-dimethyl- |
|  | Bicyclo [2.2.2] octane, 1-bromo-4-methyl |
|  | Bicyclo [2.2.2] octane, 1-methyl-4-(methylsulfonyl)- |
| 7, 9:04 | p-Menth-4(8)-en-9-ol |
|  | Cyclopropane, trimethyl (2-methyl-1-propenylidene)- |
|  | Bicyclo[6.1.0]nonane, 9-(1-methylethylidene)- |
| 8, 9:45 | cyclohexamethanol, 4(l-methylethyl)-, cis- |
|  | 3-Heptadecen-5-yne, (Z)- |
|  | 9, 1-2, 15-Octadecatrien-1-ol |
| 9, 10:11 | [4.2.2] propella-2,4,7,9-tetraene |
|  | Naphthalene |
|  | Azalene |
| 10, 11:29 | (R)-(−)-(Z)-14-Methyl-8-hexadecen-1-ol |
|  | (Z) 6-Pentadecen-1-ol |
|  | 3-Eicosyne |
| 11, 13:37 | 2-naphthalenol, decahydro- |
|  | 2) 13-octadecenal (Z)- |
|  | 3) cyclohexanol, 5-methyl-2-(1-methylethenyl)- |
| 12, 13:58 | 1,3-Benzenediol, 5-pentadecyl- |
|  | 1,3-Benzenediol, 5-pentyl- |
|  | 2-Cyclohexen-1-one, 4-hydroxy-3,5,6-trimethyl-4-(3-oxo-butenyl)- |
| 13, 14:22 | Bicyclo [2.2.1] heptane, 2-chloro-2,3,3-trimethyl- |
|  | Bicyclo [2.2.1] heptane, 2-chloro-1,7,7-trimethyl-, exo- |
|  | Bicyclo [2.2.1]heptan-2-ol, 1,3,3-trimethyl-, acetate, endo- |
| 14, 14:53 | Menth-1(8)-ene |
|  | 8-Hexadecyne |
|  | Cyclohexane, 1-methyl-4-(1-methylethylidene)- |
| 15, 15:13 | Benzene, 1-hexynyl- |

TABLE 4-continued

| Peak number, Retention time (min) | Probable composition |
|---|---|
| | Benzene, 1-cyclohexen-1-yl- |
| | Benzene, [(1-methylethylidene) cyclopropyl]-, (R)- |
| 16, 15:29 | (R) - (−) - (Z)-14-methyl-8-hexadecen-1-ol |
| | 3-Eicosyne |
| | (Z) 6-Pentadecen-1-ol |
| 17, 15:47 | Cyclopentane, 1-methyl-2-methylene- |
| | Menth-1(8)-ene |
| | Cyclohexane, 1-methyl-4-(1-methylethylidene)- |
| 18, 16:57 | 3-Acetyl-2,4,4-trimethylcyclohex-2-en-1-one |
| | Phosphonic acid, 7-octenyl-, diethyl ester |
| 20, 17:11 | N-Ethyl-6-propyl-6-dodecanamine |
| | 4H-1-Benzoselenin-4-one, 2,3-dihydro- |
| | 1H-Carbazole-Z-ethylamine, 3-ethyl-2,3,4,9-tetrahydro-N,N,1-trimethyl- |
| 21, 17:43 | 10-undecenal |
| | 13-tetradecenal |
| | undecenal |
| 22, 17:54 | Propanoic acid, 2-methyl-, 3-hydroxy-2,4,4-trimethylpentyl ester |
| | Propionic acid, 2-methyl, 2-ethyl-3-hydroxyhexyl-ester |
| | 2,4,6-Trimethyldecane-1,3,10-triol |
| 23, 18:33 | 4a(2H)-Naphthalenol, octahydro-4,8a-dimethyl-(4α, 4aα, 8αβ)- |
| | trans-1, 10-Dimethyl-trans-9-decalol |
| | 1,2-cyclohexanedicarboxaldehyde |
| 24, 19:26 | 3-Eicosyne |
| | (Z) 6-Pentadecen-1-ol |
| | Cyclohexanol, 5-methyl-2-(1-methylethyl)-, (1α,2β, 5α)- |
| 25, 20:12 | Camphorsulfonic acid |
| | 2H-Inden-2-one, 1-bromooctahydro-7a-methyl-, (3aα, 7aβ) |
| | 1H-benzocycloheptan-7-ol,2,3,4,4a,5,6,7,8-octahydro-1,1,4a,7-tetramethyl, cis- |
| 26, 21;13 | 1,6,10-Dodecatrien-3-01,3,7,11-trimethyl-(E)- |
| | Cyclohexane, 1-ethenyl-1-methyl-2-(methylethenyl)-4-1-methyl) |
| | Germacrone B |
| 27, 21:26 | 2,5-Cyclohexadiene-1,4-dione,2,6-bis (1,1-dimethyethyl)-2H-2, |
| | 4a-Ethanonaphthalen-8(5H)-one, hexahydro-2,5,5-trimethyl- |
| | 3-Buten-2-one, 4-(2,6,6-trimethyl-1-cyclohexen-1-yl)- |
| 28, 22:08 | phenol, (1,1-dimethylethyl)-2-methoxyl |
| | Benzenethiol,4-(1,1-dimethylethyl)-2-methyl- |
| 31, 25:57 | γ-Gurjunene |
| | 1H-cycloprop[e]azulene, decahydro-1,1,7-trimethyl-4-methylene-, |
| | [-]-A-Selinene |
| 32, 29:35 | Cyclohexane, (2,2-dimethylcyclopentyl)- |
| | Cyclopentadecenol |
| | (Z) 6-Pentadecen-1-ol |
| 33, 30:14 | Altretamine |
| | 1,1-Biphenyl,2,2-diethyl- |
| 34, 30:30 | Heptadecane, 2,6,10,15-tetramethyl |
| | Tritetracontane |
| | Hexadecane, 2,6,11,15-tetramethyl |
| 35, 30:42 | 1-Dotriacontanol |
| | Heneicosyl formate |
| | 1-Hexadecanol, 3,7,11,15-tetramethyl- |
| 36, 30:52 | 2(1H)-Benzocyclooctenone, decahydro-10a-methyl, -trans Benzocyclodecane, tetradecahydro-9-Eicosyne |
| 37, 31:27 | 1,1-Biphenyl, 2,2'-diethyl- |
| | Benzene, 1,1'-methylenebis[4]-methyl- |
| | Benzene 1,2-dimethyl-4-(phenylmethyl)- |

EXAMPLES 74–84

By taking samples from air pumped from a termite nest, other volatile compounds from termite nests have been identified. One end of a Tenax™ short path thermal desorption tube was connected to a pump. The other end of the tube was connected to metal tubing, which was in turn inserted into a termite nest. After 30 minutes, the pump was turned off, and the sample was analyzed by a GC-MS instrument equipped with a short path thermal desorption apparatus. The volatile compounds thus identified included the following:

δ-3-carene 2,3,7-trimethyloctane 2,6, 10-trimethyldodecane elemene

α-longipinene aristolene calarene

β-guaiene

N-(1-methylhexylidene)-methylamine 2,6,10,14-tetramethylpentadecane

α-muurolene fenchone

The last item on this list, fenchone, is known to have properties as an insecticide and fumigant. As with naphthalene, termites may use fenchone to repel other organisms such as ants from the nest.

In a preferred embodiment, an effective amount of a feeding stimulant comprising one or more of the compounds selected from the group consisting of DBP, naphthalene, hexanedioic acid dioctyl ester, and dioctyl phthalate are mixed with a toxicant for termites, preferably by impregnating both the stimulant and the attractant into a termite bait such as cardboard. Other preferred feeding stimulants include ergosterol and its analogs (such as steroids specific to yeasts and other fungi). Preferred attractants that may be used in conjunction with feeding stimulants include 2-phenoxyethanol; naphthalene; 3,5-di-tert-butyl-1,2-benzoquinone; 1,1-dimethylethyl-2-methoxyphenol; and 3-carene and its analogs (such as wood-derived terpenes). When the impregnated bait is placed in the vicinity of a termite colony, termites will preferentially feed on the treated bait, thereby consuming the toxicant, and typically thereafter introducing the toxicant to other members of the colony as well. Not only do these stimulants increase feeding activity, but they can also increase the durability of the bait: (1) by excluding natural enemies of termites (such as fire ants) from the bait; and (2) by inhibiting deterioration of the bait matrix material. BHT is an antioxidant and preservative. Naphthalene is a common arthropod fumigant, antiseptic, and anthelmintic agent; dioctyl phthalate and hexanedioic acid dioctyl ester are antimicrobial agents. Despite these activities, these agents are naturally associated with termites. Thus use of these agents in termite bait can both increase bait acceptance, and increase durability of the bait. No single compound has previously been reported to have such dual activity in a termite bait.

Optionally, one or more free amino acids may also be added to the termite baits to further stimulate feeding, preferably aspartic acid, glutamic acid, or proline. See U.S. patent application Ser. No. 08/243,950, filed May 17, 1994.

Formosan termites deposit BHT on their food, presumably to help preserve it. We have observed that BHT is even more effective than naphthalene at killing ants. BHT may also help preserve termite trail pheromone. The instability of the trail pheromone has previously been a limiting factor in the use of pheromones or trail-following substances in termite baits. Adding BHT or another antioxidant to known pheromones will allow pheromones or trail-following substances to be used in baits.

An alternative is to place a volatile attractant or feeding stimulant behind a semi-permeable membrane, so that the volatile attractant or stimulant "leaks" out slowly in the field. Examples of suitable semi-permeable membranes include parafilm, paper, waxed paper, nitrocellulose, nylon 66, and gelatin.

Another application of this invention is to detect carton-associated compounds in the field, to identify the presence and location of termite nests. For example, naturally-occurring naphthalene is rare in most areas. Thus field detection of naphthalene can be a fairly specific indication of the presence of a termite nest (after excluding, if necessary, artificial sources of naphthalene such as moth balls). Field detection may be performed, for example, with a portable gas chromatograph such as that disclosed in U.S. Pat. No. 5,611,846.

A related application is to trap volatile compounds over a period of time, e.g. over a period of hours to months, and have the trapped volatiles analyzed by an off-site laboratory for reporter molecules indicating the possible presence of a termite colony. For example, an inexpensive device for this purpose could be placed in the home, comprising a small air pump and a trap made from an absorbent material such as Tenax™. Other suitable adsorbents include silica gel, Hopcalite™, charcoal, and polyethylene foam. In a preferred embodiment, the sampling device is adapted to pump air from the interior of a wall, floor, ceiling, roof, or eave through an electrical, telephone, cable, or lighting outlet, or through a vent. The air from the interior of a wall is likely to have higher concentrations of volatile compounds associated with termite nests, both because termite nests and shelter tubes tend to be found in such regions, and also because air circulation is lower in these confined spaces. Pumping air from an existing outlet or vent avoids the need to drill holes into walls to sample such areas. Preferably, the pump and adsorbent are incorporated into a small unit that plugs into and remains in place in an electrical socket, superficially similar to units such as carbon monoxide detectors sold for use in the home. Air is drawn from a second socket in the same electrical outlet, for example through a cup positioned over the second socket, or through non-conductive tubes shaped to be inserted into the socket and pull air from inside the outlet. The pump is preferably operated by current from the same outlet; but alternatively could be operated by batteries. In an alternative embodiment, an adapter holding the adsorbent is mounted onto a vacuum cleaner, and the vacuum cleaner acts as the pump to pull air from the interior region across the adsorbent.

In household applications, naphthalene is preferred reporter molecule. Other volatile compounds identified in the nest may also be used, including terpenes and terpenoids. Of these compounds, fenchone appeared in our data most consistently, and is considered especially promising.

Naphthalene has never previously been reported to occur naturally in association with termites, nor indeed with any insects or other invertebrates. Naphthalene at concentrations of 0.1 to 0.5 mg/kg (or more) in termite cartons may constitute (at least in part) a unique chemical defense strategy. A termite nest is a partially closed system that protects termites from air movement and provides a controlled microclimate. This semi-closed system may allow termites to use fumigation as a defense strategy. Such nest fumigation may repel invertebrates and other animals from entering the carton nests. In fact, we have found that Formosan subterranean termites have a higher tolerance to naphthalene than that of one of their natural enemies, ants.

We have compared the effect of naphthalene on *C. formosanus* and on the imported red fire ant, *Solenopsis invicta* Buren. We found that *C. formosanus* had significantly higher tolerance to naphthalene than did *S. invicta*. Ants were paralyzed at naphthalene concentrations that caused no visible effect on termites. Naphthalene fumigation of nests may play an important role in defending termite nests from predation by ants.

Naphthalene is an antimicrobial and anthelmintic agent. Soil-dwelling Formosan termites confront many adversaries, including ants, fungi, bacteria, and nematodes. Ants are known to secrete compounds with antimicrobial ability to help them succeed in soil habitats. Formosan subterranean termites may use a similar strategy. Fumigating the nest with naphthalene may play an important role in inhibiting microorganisms and nematodes.

The origin of the naphthalene in nest carton is currently unknown. Naturally-occurring naphthalene has previously been reported from coal, petroleum, incomplete combustion of organic materials from forest fires, and Magnolia flowers. Naphthalene is a common arthropod fumigant (e.g., against clothes moths), and has been used as a repellent against bats, pigeons, sparrows, squirrels, starlings, and rabbits. Since termites use soil, masticated wood, and excrement to make their nests, a possible source of naphthalene is processed food or soil. However, a literature search indicated that naphthalene is not present in wood, although wood does contain several potential precursors for naphthalene. Naphthalene has never been reported as a natural constituent of any type of soil. Although the possibility of soil pollution with naphthalene cannot be excluded, it seems unlikely that the widely dispersed termite nests examined in these experiments were all contaminated by artificial sources of naphthalene. Another possible origin for naphthalene is microbial biosynthesis in the termite nest, gut, or on the food. However, a literature search found no prior reports of naphthalene biosynthesis by any microorganisms or invertebrates.

As used in the specification and in the claims, an "effective amount" of a feeding stimulant is an amount that, when mixed with a termite toxicant in a bait, will increase the rate of consumption of the toxicant by termites to at least ten percent above the rate of consumption of an otherwise comparable bait lacking the feeding stimulant.

As used in the specification and in the claims, an "effective amount" of an attractant is an amount that, when placed in the vicinity of a bait containing a termite toxicant in a bait, will increase the rate of consumption of the toxicant by termites to at least ten percent above the rate of consumption of an otherwise identical bait placed in the absence of the attractant.

Preferred toxicants are slow-acting, to avoid "learning" effects before individuals have distributed food to other members of the colony. Several slow-acting toxicants for termites are known in the art, and include, for example sulfluramid, avermectin, hydramethylnon, hexaflumuron, fipronil, and diflubenzuron.

Preferred termite bait materials include cardboard, paper, sugar cane, corn cobs, and dried semi-aqueous cellulose mixtures. An alternative to impregnation of the bait is to manufacture paper or cardboard containing the toxicant and feeding stimulant in the paper or cardboard from the beginning. Adding moisture to the bait can help increase its attractiveness to termites. Attractants (especially water-soluble attractants) may optionally be added to the soil to draw termites towards the bait.

The complete disclosures of all references cited in this specification are hereby incorporated by reference. In the event of an otherwise irreconcilable conflict, however, the present specification shall control.

We claim:

1. A process for locating a termite nest in a building or the vicinity of a building, comprising analyzing air samples in the building or the vicinity of the building for the presence of at least one reporter molecule at a concentration higher than the background concentration of the reporter molecule, if any, generally prevailing in the area of the building; and, if a region of such higher concentration is identified, searching the region of higher concentration for the presence of a termite nest; wherein the reporter molecule is selected from the group consisting of naphthalene; δ-3-carene; 2,3,7-trimethyloctane; 2,6,10-trimethyldodecane; elemene; α-longipinene; aristolene; calarene; β-guaiene; N-(1-methylhexylidene)-methylamine; 2,6,10,14-tetramethylpentadecane; α-muurolene; and fenchone.

2. A process as recited in claim 1, wherein the reporter molecule is naphthalene.

3. A process as recited in claim 1, wherein the reporter molecule is fenchone.

4. A process as recited in claim 1, wherein volatile compounds from air samples in the area are trapped over a period of time, and wherein the trapped volatile compounds are analyzed at a site not in physical proximity to the area.

5. A process as recited in claim 1, wherein the reporter molecule is δ-3-carene.

6. A process as recited in claim 1, wherein the reporter molecule is 2,3,7-trimethyloctane.

7. A process as recited in claim 1, wherein the reporter molecule is 2,6,10-trimethyldodecane.

8. A process as recited in claim 1, wherein the reporter molecule is elemene.

9. A process as recited in claim 1, wherein the reporter molecule is α-longipinene.

10. A process as recited in claim 1, wherein the reporter molecule is aristolene.

11. A process as recited in claim 1, wherein the reporter molecule is calarene.

12. A process as recited in claim 1, wherein the reporter molecule is β-guaiene.

13. A process as recited in claim 1, wherein the reporter molecule is N-(1-methylhexylidene)-methylamine.

14. A process as recited in claim 1, wherein the reporter molecule is 2,6,10,14-tetramethylpentadecane.

15. A process as recited in claim 1, wherein the reporter molecule is α-muurolene.

* * * * *